United States Patent [19]

Takematsu et al.

[11] Patent Number: 4,749,812

[45] Date of Patent: Jun. 7, 1988

[54] N-(3-CHLORO-4-ISOPROPYLPHENYL) CARBOXAMIDE DERIVATIVE AND SELECTIVE HERBICIDE

[75] Inventors: Tetsuo Takematsu, Utsunomiya; Mitihihiko Nakaya, Zushi; Koichi Moriyasu, Yokohama, all of Japan

[73] Assignee: Mitsui Toatsu Chemicals, Inc., Tokyo, Japan

[21] Appl. No.: 865,437

[22] Filed: May 21, 1986

[30] Foreign Application Priority Data

May 27, 1985 [JP] Japan .................. 60-112087
May 31, 1985 [JP] Japan .................. 60-116591

[51] Int. Cl.$^4$ .................. C07C 103/34; A01N 37/18
[52] U.S. Cl. .................. 564/218; 564/190; 71/118
[58] Field of Search .................. 564/190, 218; 71/118

[56] References Cited

U.S. PATENT DOCUMENTS

| | | | |
|---|---|---|---|
| 2,655,444 | 10/1953 | Todd | 71/2.6 |
| 2,655,445 | 10/1953 | Todd | 71/2.6 |
| 2,756,135 | 7/1956 | Searle | 71/2.5 |
| 2,906,614 | 9/1959 | Hopkins et al. | 71/2.6 |
| 2,960,534 | 11/1960 | Scherer et al. | 260/553 |
| 3,277,107 | 10/1966 | Nieghbors | 260/306.8 |
| 3,277,171 | 10/1966 | Hopkins | 260/557 |
| 3,332,768 | 7/1967 | Freund et al. | 71/118 |
| 3,407,056 | 10/1968 | Schwartz | 71/118 |
| 3,784,635 | 1/1974 | Theissen | 260/471 R |
| 3,816,092 | 6/1974 | Wilson et al. | 71/118 |
| 4,127,405 | 11/1978 | Levitt | 71/93 |
| 4,166,735 | 9/1979 | Pilgram et al. | 71/118 |
| 4,427,596 | 1/1984 | Takemoto et al. | 564/190 X |
| 4,447,260 | 5/1984 | Noguichi et al. | 564/190 X |
| 4,517,387 | 5/1985 | Matsunaga et al. | 568/728 |

FOREIGN PATENT DOCUMENTS

| | | |
|---|---|---|
| 1000632 | 6/1957 | Fed. Rep. of Germany ...... 564/218 UX |
| 1166547 | 3/1964 | Fed. Rep. of Germany ...... 564/218 UX |
| 1913850 | 10/1970 | Fed. Rep. of Germany ...... 564/218 UX |
| 2107774 | 9/1971 | Fed. Rep. of Germany ...... 564/218 UX |
| 2137992 | 2/1972 | Fed. Rep. of Germany ...... 564/218 UX |
| 2223894 | 5/1972 | Fed. Rep. of Germany ...... 568/218 UX |
| 2232263 | 1/1973 | Fed. Rep. of Germany ...... 564/218 UX |
| 2249547 | 4/1974 | Fed. Rep. of Germany ....... 71/118 |
| 2441504 | 3/1975 | Fed. Rep. of Germany ...... 564/218 UX |
| 1497867 | 9/1967 | France .................. 564/218 UX |
| 1497868 | 9/1967 | France .................. 564/218 UX |
| 2377999 | 8/1978 | France .................. 71/118 |
| 193806 | 11/1984 | Japan .................. 564/218 UX |
| 23357 | 2/1985 | Japan .................. 564/218 UX |
| 6717715 | 7/1968 | Netherlands .................. 564/218 UX |
| 793513 | 4/1958 | United Kingdom ........ 564/218 UX |
| 869169 | 5/1961 | United Kingdom ........ 564/218 UX |
| 885048 | 12/1961 | United Kingdom ........ 564/218 UX |
| 1132306 | 10/1968 | United Kingdom ........ 564/218 UX |

OTHER PUBLICATIONS

European Search Report-EP 86303956.
P. W. Zimmerman and A. E. Hitchcock—Contrib. Boyce Thompson Inst. 12, 321 (1942) "Substituted Phenoxy and Benzoic Acid Grown Substances and the Relation of Structure to Physiological Activity".
Chemical Abstracts, vol. 70, (1969) p. 362—(An Abstract of S.A. Patent No. 6,705,164).
C. W. Hoffman et al., J. Agric. Food Chem., 8, 298 (1960) "Molecular Size Vs. Herbicidal Activity of Anilides".
M. E. Synerhold and P. W. Zimmerman—Contrib. Boyce Thompson Inst., 14, 369 (1945) "Preparation of a Series of ω-(2,4-Dichlorophenoxy)-Aliphatic Acids and Some Related Compounds with a Consideration of Their Biochemical Role as Plant-Growth Regulators".
M. E. Synerholm and P. W. Zimmerman—Contrib. Boyce Thompson Inst., 14, 91 (1945) "The Preparation of Some Substituted Phenoxy Alkyl Carboxylic Acids and Their Properties as Growth Substances".

Primary Examiner—Paul F. Shaver
Attorney, Agent, or Firm—Fisher, Christen & Sabol

[57] ABSTRACT

An N-(3-chloro-4-isopropylphenyl)carboxamide derivative represented by the general formula

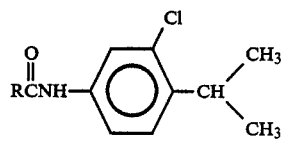

wherein R represents a 1-methylbutyl, 1-methylcyclopropyl or cyclopropyl group. This derivative is useful as a selective herbicide, and can be produced by reacting 3-chloro-4-isopropylaniline with a carboxylic acid halide derivative of the general formula

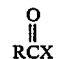

wherein R is as defined above and X represents halogen, or with a carboxyilc acid anhydride of the general formula

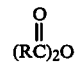

wherein R is as defined above.

2 Claims, No Drawings

N-(3-CHLORO-4-ISOPROPYLPHENYL) CARBOXAMIDE DERIVATIVE AND SELECTIVE HERBICIDE

This invention relates to an N-(3-chloro-4-isopropyl)-carboxamide derivative, and a selective herbicide comprising it as an active ingredient which controls noxious weeds in the cultivation of wheat, an important gramineous crop in agriculture, effectively and selectively by foliar application.

For a control of weeds in wheat cultivation, phenoxy-type herbicides have been used most widely. They include, for example, 2,4-dichlorophenoxyacetic acid [2,4-D; P. W. Zimmerman and A. E. Hitchcock, Contrib. Boyce Thompson Inst., 12, 321 (1942)], 2-methyl-4-chlorophenoxyacetic acid [MCPA; M. E. Synerholm and P. W. Zimmerman, Contrib. Boyce Thompson Inst., 14, 91 (1945)], 4-(2-methyl-4-chlorophenoxy)butyric acid [MCPB; German Pat. No. 1,000,632 (1957) and British Pat. No. 793,513 (1958)], and 4-(2,4-dichlorophenoxybutyric acid [2,4-DB; M. E. Synerholm and P. W. Zimmerman, Contrib. Boyce Thompson Inst , 14, 369 (1945)]. However, these herbicides are foliar treating agents which are effective only for controlling broad-leaved weeds, and because of their significant phytotoxicity to wheat, their use is limited only to a stage where the crop has grown to some extent.

Urea-type herbicides such as 3-(3,4-dichlorophenyl)-1-methoxy-1-methylurea [linuron; U.S. Pat. No. 2,960,534 issued Nov. 15, 1960], 3-(3-chloro-4-methoxyphenyl)-1,1-dimethylurea [metoxuron; French Pat. Nos. 1,497,867 and 1,497,868 granted Oct. 13, 1967], 3-(3-chloro-4-methylophenyl)-1,1-dimethylurea [chlortoluron; U.S. Pat. Nos. 2,655,444 and 2,655,445 issued Oct. 13, 1953], 3-(4-isopropylphenyl)-1,1-dimethylurea [isoproturon; German OLS 2,107,774 published Sept. 16, 1971, and German OLS 2,137,992 published Feb. 10, 1972], and 3-(2-benzothiazolyl)-1,3-dimethylurea [methabenzthiazuron; U.S. Pat. No. 2,756,135 issued July 24, 1956 and British Pat. No. 1,085,430 patented Oct. 4, 1967] are very important in wheat cultivation. Since, however, most of them cause phytotoxicity to the crop, they are used mainly as a preemergence soil treating agent. When they are used as a foliar treating agent, their selectivity differs greatly depending upon the variety of wheat, the cultivation conditions, etc. Moreover, their herbicidal spectrum does not cover all hazardous weeds in wheat cultivation, and they are usually applied as mixtures.

Attempts have been made to apply 2-(2-chloro-4-ethylamino-s-triazin-6-ylamino)-2-methylpropionitrile [cyanazine; British Pat. No. 1,132,306 patented Oct. 30, 1968], 3,4-dimethyl-2,6-dinitro-N-(1-ethylpropyl)aniline [pendimethalin; German OLS 2,232,263 published Jan. 11, 1973], alpha,alpha,alpha-trifluoro-2,6-dinitro-N-(2-chloroethyl)-N-propyl-p-toluidine [fluchloralin; German OLS 2,161,879 published June 20, 1973], and 2,4-dichlorophenyl-3-methoxycarbonyl-4-nitrophenylether [bifenox; U.S. Pat. No. 3,784,635 issued Jan. 8, 1974] as herbicides for controlling weeds in wheat cultivation. They are also used as mixtures, and when used singly, they exhibit only an insufficient efficacy against many hazardous weeds.

4-Chloro-2-butynyl-N-(3-chlorophenyl) carbamate [barban; U.S. Pat. No. 2,906,614 issued Sept. 29, 1959], N-benzoyl-N-(3,4-dichlorophenyl)-2-aminopropionic acid ethyl ester [benzoylprop-ethyl; Dutch Patent Application 6,717,715 filed July 1, 1968], 1,2-dimethyl-3,5-diphenyl-1H-pyrazolium methyl sulfate [difenzoquat; German OLS 2,441,504 published Mar. 20, 1975]and (±)-2-[4-(2,4-dichlorophenoxy)phenoxy]propionic acid methyl ester [diclofop-methyl; German OLS 2,223,894 published Dec. 13, 1973] are applied as agent for exclusively combatting wild oats, a very strongly hazardous weed, but their practical effect is not sufficient.

Other herbicides for wheat cultivation include, for example, 3-isopropyl-1H-2,1,3-benzothiazin-(4)-3H-one-2,2-dioxide [bentazon; South African Pat. No. 6,705,164 patented Jan. 23, 1968 and German OLS 1,913,850 published Oct. 1, 1970] and 2-chloro-N-(4-methoxy-6-methyl-1,3,5-triazin-2-yl-aminocarbonyl)-benzenesulfonamide [chlorsulfuron; U.S. Pat. No. 4,127,405 issued Nov. 28, 1978] which has recently aroused interest as a highly active compound. The former is a compound having high safety to wheat, but its application is limited to certain broad-leaved weeds. The latter has an excellent soil treating effect at very low dosages with an outstanding residual activity, and also is highly safe to wheat. However, even at low dosages, it is likely to cause phytotoxicity to crops grown in wheat fields after harvesting wheat. Accordingly, its use is greatly restricted. Nowadays, agricultural chemicals are required not only to have excellent activity but also to have high safety against humans and animals and their environment.

Much work has been undertaken on N-phenylcarboxylic acid amide derivatives over many years, and various excellent herbicides of this type have been known and used. They are disclosed, for example, in C. W. Hoffman et al., J. Agric. Food Chem., 8, 298 (1960) [N-(3,4-dichlorophenyl)propionamide; propanil], British Pat. No. 869,169 patented May 31, 1961 [karsil, solan], German Pat. No. 1,166,547 patented May 26, 1964 [monalide], U.S. Pat. No. 3,816,092 issued June 11, 1974, British Pat. No. 885,043 patented May 4, 1959 [DCMA; dicryl], U.S. Pat. No. 3,277,107 issued Oct. 4, 1966 [cypromid], U.S. Pat. No. 4,166,735 issued Sept. 4, 1979, and U.S. Pat. No. 3,277,171 issued Oct. 4, 1966. Many of these compounds kill weeds very effectively in foliar treatment and show a high level of selectivity for certain kinds of important crops. These compounds are also expected to decompose comparatively rapidly, and it is anticipated to some extent that their effect on crops to be grown after harvesting will be small and they will have little residual effects in the environment. Many of these prior art references, however, fail to disclose the selectivity of these compounds for wheat. The selectivities of compounds, which are disclosed in some of these references, are insufficient, or such compounds have an insufficient herbicidal efficacy. In fact, the compounds disclosed in these prior art references are difficult to use in actual wheat cultivation.

Japanese Patent Publication No. 14240/1966 published on Aug. 9, 1966 and German OLS 2,249,547 published on Apr. 18, 1974 disclose the selectivity of N-phenylcarboxylic acid amide derivatives for wheat, but these compounds are not entirely satisfactory in their herbicidal efficacy against weeds and their phytotoxicity to crops. In particular, German OLS 2,249,547 disclose compounds of the following general formula

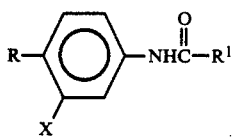

wherein R represents an alkyl group having 2 to 6 carbon atoms, $R^1$ represents an alkyl group having 2 to 8 carbon atoms, an alkenyl group having 3 to 6 carbon atoms or a cycloalkyl group having 3 to 8 carbon atoms, and X represents a halogen atom.

A very few specific compounds, however, are actually cited in the specification as examples of the above compounds, and when R is an isoporopyl group, only an ethyl group is shown as an example of $R^1$. Furthermore, these compounds are not practically feasible for the reason given above.

Japanese Laid-Open Patent Publication No. 193806/1984 published on Nov. 2, 1984 and Japanese Laid-Open Patent Publication No. 23357/1985 published on Feb. 5, 1985 disclose N-(4-isopropylphenyl)-carboxyamide derivatives. These compounds, however, have the defect that their effects are unstable and they do not show herbicidal activity on some important weeds.

It has been strongly desired therefore to develop a chemical having essential selectivity for weeds in the cultivation of important gramineous crops, particularly wheat, a chemical which is little affected by physical factors such as soil conditions (i.e., foliar treating agents), a chemical which shows an efficacy in low dosages and has a broad herbicidal spectrum ranging from gramineous weeds to broad-leaved weeds, and a chemical which rapidly decomposes and does not exert deleterious effects such as environmental pollution.

It is an object of this invention to provide a herbicide whose efficacy or phytotoxicity does not depend upon physical factors such as soil conditions in the cultivation of wheat which is an important gramineous crop.

A more specific object of this invention is to provide a highly selective herbicide which has essential selectivity for an important gramineous crop, particularly wheat, and produces an accurate control efficacy by simple foliar treatment in low dosages.

The present inventors studied many compounds in order to develop a highly selective herbicide for important gramineous crops, particularly wheat, and have now found that in foliar treatment, N-(3-chloro-4-isopropylphenyl)carboxamide derivatives have an excellent selective herbicidal action and has a very broad herbicidal spectrum while causing no phytotoxicity to important gramineous crops, particularly wheat, even when applied in very high concentrations, and that these compounds solve the various problems described above.

Generally, compounds of the same series or structurally similar compounds are thought to have similar properties. But actually, it is not easy to infer such properties, and for example, by simply increasing the alkyl chain of one substituent in a herbicidal compound, the herbicidal activity of the compound against weeds or its phytotoxicity to crops varies greatly.

The N-(3-chloro-4-isopropylphenyl)carboxamide derivatives in accordance with this invention are novel compounds represented by general formula (I) below

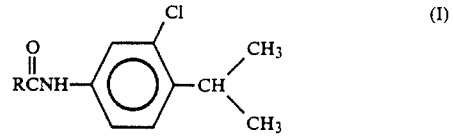

wherein R is a 1-methylbutyl, 1-methylcyclopropyl or cyclopropyl group.

A herbicide comprising an N-(3-chloro-4-isopropylphenyl)carboxamide derivative in accordance with this invention having general formula (I) as an active ingredient, when applied by foliar treatment, very effectively controls almost all hazardous upland farm weeds, for example strongly hazardous gramineous weeds such as wild oats (*Avena fatua*), meadow foxtail (*Alopecurus pratensis*), blackgrass (*Alopecurus myosuroides*), annual bluegrass (*Poa annua*), water foxtail (*Alopecurus aequalis*), barnyard grass (*Echinochloa oryzicola*), crabgrass (*Diqitaria ciliaris*) and green foxtail (*Setaria viridis*); and strongly hazardous weeds such as green amaranth (*Amaranthus retroflexus*), common purslane (*Portulaca oleracea*), cocklebur (*Xanthium strumarium*), cleavers (*Galium spurium*), lamb's quarters (*Chenopodium album*), chickweed (*Stellaria media*), tall morning glory (*Ipomea purpurea*), *Cerastium holosteoides*, velvet leaf (*Abutilon theophrasti*), oriental senna (*Cassia obtusifolia*), pick purse (*Capsella bursapastoris*), charlock (*Sinapis arvensis*), dayflower (*Commelina communis*), johnson grass (*Sorghum helepense*), speedwell (*Veronica persica*), *Veronica caninotesticulate*, hairly galinsoga (*Galinsoga ciliata*), common groundsel (*Senecio vulgaris*), matricaria (*Matricaria chamomilla*), and *Urtica*. A compound of formula (I) in which R is 1-methylbutyl is preferred in respect of the stability of its effect. On the other hand, no phytotoxicity of this herbicide to important gramineous crops, particularly wheat, is observed.

Thus, the N-(3-chloro-4-isopropylphenyl)carboxamide derivatives of this invention have essential foliar treatment selectivity in the cultivation of important gramineous crops, particularly wheat, and can be very safely used. Various herbicides now in use in the cultivation of wheat are soil treating agents. The defects of these herbicides, that is, variations in efficacy and phytotoxicity owing to physical factors such as soil conditions, are not at all observed in the herbicide of this invention. Furthermore, the herbicide of this invention has little effects on crops cultivated in the same field after harvesting of wheat.

The N-(3-chloro-4-isopropylphenyl)carboxamide derivative in accordance with this invention is a novel compound, and can be easily produced by reacting 3-chloro-4-isopropylaniline with a carboxylic acid halide derivative of general formula (II) or a carboxylic acid anhydride derivative of general formula (III) in accordance with the following scheme.

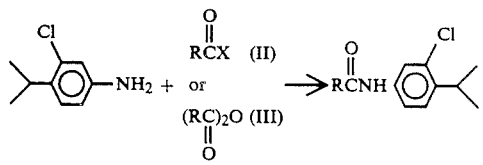

(In the above scheme, R represents a 1-methylbutyl, 1-methylcyclopropyl or cyclopropyl group, and X represents a halogen atom.)

The reaction is carried out in the absence of solvent or in an inert solvent. Examples of the inert solvent include aromatic hydrocarbons such as benzene, toluene, xylene, chlorobenzene and dichlorobenzene, ketones such as acetone and methyl ethyl ketone, nitriles such as acetonitrile and propionitrile, ethers such as ethyl ether, tetrahydrofuran and dioxane, and aprotic polar solvents such as dimethylformamide, dimethyl sulfoxide and hexamethylphosphoramide. In using the acid halide or acid anhydride, an organic base such as triethylamine, pyridine, dimethylaniline or 1,8-diazabicyclo(5,4,0)-7-undecene or an inorganic base such as potassium carbonate, sodium carbonate, sodium hydroxide, potassium hydroxide or sodium hydrogen carbonate may be used, as required, as an acid binder. The reaction temperature is −10° to 150° C., preferably 5°0 to 90° C., more preferably 15° to 70° C. The reaction may also be carried out at the refluxing temperature of the solvent used. The reaction time differs according to the reaction temperature or the solvent used. Generally, it is 1 second to 10 hours, preferably 1 minute to 5 hours, more preferably 20 minutes to 3 hours.

The rate of application of the N-(3-chloro-4-isopropylphenyl)-carboxamide derivative of this invention can be selected according to the extent to which the growth of weeds is required to be inhibited. The standard rate of application is 0.1 to 10 kg per hectare, preferably 0.2 to 3 kg per hectare.

The herbicide of this invention comprises the compound of general formula (I) as a main ingredient. The compound of formula (I) may be directly used against plants to be treated. Generally, however, it is used in usual formulations containing a carrier and as required other adjuvants, for example as a dust, granules, a wettable powder, an emulsifiable concentrate or a flowable agent.

Examples of the carrier are inorganic materials such as clays, talc, bentonite, calcium carbonate, diatomaceous earth, zeolite and silicic anhydride, organic materials of plant origin such as wheat flour, soybean meal, starch and crystalline cellulose, polymeric compounds such as petroleum resins, polyvinyl chloride and polyalkylene glycols, urea, and waxes. Liquid carriers such as oils, organic solvents and water may also be used.

Examples of the adjuvants are a wetting agent, a dispersing agent, a sticker, and a spreader which may, as required, be used either singly or in combination.

Various surface-active agents, polymeric compounds such as gelatin, albumin, sodium alginate, methyl cellulose, polyvinyl alcohol and xanthan gum, and other adjuvants may be cited as auxiliary agents which are used for the purpose of wetting, dispersion, spreading, stabilization of components or stabilization of properties. Industrial fungicides, bactericides and moldproofing agents may be added to flowable agents for killing fungi, bacteria or molds.

The surface-active agents may be nonionic, anionic, cationic and amphoteric. Examples of preferred surface-active agents include products of polymerization of ethylene oxide with alkylphenols, higher alcohols, alkylnaphthols, higher fatty acids, fatty acid esters or dialkylphosphoric acid amines, a copolymer of ethylene oxide and propylene oxide, alkylsulfuric acid ester salts (such as sodium laurylsulfate), alkylsulfonic acid salts (sodium 2-ethylhexenesulfonate), and arylsulfonic acid salts (such as sodium ligninsulfonate, and sodium dodecyl- benzenesulfonate).

The content of the compound of general formula (I) in the herbicide of this invention differs depending upon the formulation, and usually is 1 to 20% by weight for a dust, 20 to 90% by weight for a wettable powder, 1 to 30% by weight for granules, 1 to 50% by weight for an emulsifiable concentrate, 10 to 90% by weight for a flowable agent, and 20 to 70% by weight for a dry flowable agent. The content of the adjuvants is 0 to 80% by weight, and the amount of the carrier is obtained by subtracting the contents of the active compound and the adjuvants from 100% by weight.

The herbicide of this invention may be applied in admixture with at least one other herbicide, other agricultural chemicals such as an insecticide or a plant growth regulator, a soil conditioner, and a fertilizer substance, or may be formulated into a mixed agent with such other chemicals. Sometimes, this manner of application is expected to give a synergistic effect.

The following examples illustrate the present invention more specifically.

SYNTHESIS EXAMPLE 1

Production of N-(3-chloro-4-isopropylphenyl)-2-methylvaleramide

To 36 ml of toluene were added 1.0 g (5.9/1000 mole) of 3-chloro-4-isopropylaniline and 0.7 g of pyridine, and 0.9 g (5.9/1000 mole) of 2-methylvaleryl chloride was added. The mixture was stirred at room temperature for 20 minutes. The crystals that precipitated were separated by filtration. Water (70 ml) was added to the filtrate, and the mixture was extracted with toluene. The toluene solution was washed with a saturated aqueous solution of sodium hydrogen carbonate, and dried over anhydrous sodium sulfate. The resulting dried solution was concentrated by an evaporator. Recrystallization of the resulting crude crystals from methanol gave 1.2 g of N-(3-chloro-4-isopropylphenyl)-2-methylvaleramide in a yield of 76.0 % based on 3-chloro-4-isopropylaniline.

SYNTHESIS EXAMPLE 2

Production of N-(3-chloro-4-isopropylphenyl)-1-methylcyclopropanecarboxamide

To 90 ml of benzene were added 1.0 g (5.9/1000 mole) of 3-chloro-4-isopropylaniline, 0.7 g of triethylamine, and 0.8 g (6.8/1000 mole) of 1-methylcyclopropanecarboxylic acid chloride. The mixture was stirred for 1 hour at 5° to 10° C. The precipitated crystals were separated by filtration, and the filtrate was washed with a saturated aqueous solution of sodium hydrogen carbonate and dried over anhydrous sodium sulfate. The resulting dried filtrate was concentrated by an evaporator. The resulting oily product was isolated and purified by silica gel column chromatography [eluent: benzene/ethyl acetate=40/1 (v/v)] to give 1.3 g of N-(3-chloro-4-isopropylphenyl)-1-methylcyclopropanecarboxamide as an oil in a yield of 87.6 % based on 3-chloro-4-isopropylaniline. On standing for a long period of time, the oil crystallized.

SYNTHESIS EXAMPLE 3

Production of N-(3-chloro-4-isopropylphenyl) cyclopropanecarboxamide

To 20 ml of dimethylformamide were added 1.0 g (5.9/1000 mole) of 3-chloro-4-isopropylaniline and 0.5 g of potassium carbonate, and 1 g (6.5/1000 mole) of cyclopropanecarboxylic anhydride was added. The mixture was stirred under ice cooling. Three hours later, 80 ml of water was added to the reaction mixture, and the mixture extracted with toluene. The toluene solution was dried over anhydrous magnesium sulfate, and then concentrated by an evaporator. The resulting oily product was isolated and purified by silica gel column chromatography [eluent: toluene/ethyl acetate=30/1 (v/v)] to give 1.2 g of N-(3-chloro-4-isopropylphenyl)cyclopropanecarboxamide as a solid in a yield of 85.6 % based on 3-chloro-4-isopropylaniline.

The compounds of general formula (I) in accordance with this invention and their physical properties are shown in Table 1. The active ingredient compounds used in the following Formulation Examples and Test Examples are designated by the compound numbers given in Table 1.

TABLE 1

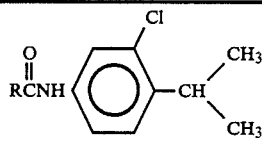

| Compound No. | R in formula (I) | Physical properties |
|---|---|---|
| 1. | 1-methylbutyl<br><br>CH₃CH₂CH₂CH—<br>                           \|<br>                           CH₃ | $IR\nu_{max}^{KBr}$ cm$^{-1}$: 3300, 1660.<br>$NMR\delta_{TMS}^{CCl_4}$: 0.86(3H, t, J=7Hz), 1.12(3H, s), 1.20(6H, d, J=7Hz), 1.24–1.76(4H, m), 2.48 (1H, m), 3.32(1H, m), 7.08(1H, d, J=8Hz), 7.40(1H, dd, J=8Hz, J=2Hz), 7.60(1H, d, J=2Hz) 9.22(1H, bs).<br>m.p.: 66.0–68.0° C.<br>Elemental analysis (%):<br>  Calc (%) C;67.27, H;8.28, N;5.23, Cl;13.24<br>  Found (%) C;67.07, H;8.57, N;5.17, Cl;13.05 |
| 2. | 1-methylcyclopropyl<br><br>CH₂\\<br>    C—<br>CH₂/ \|<br>      CH₃ | $IR\nu_{max}^{film}$ cm$^{-1}$: 3400, 1650.<br>$NMR\delta_{TMS}^{CCl_4}$: 0.57(2H, m), 1.20(2H, m), 1.22(6H, d, J=7Hz), 1.40(3H, s), 3.32(1H, m), 7.15(1H, d, J=9Hz), 7.39(1H, dd, J—9Hz, J=2Hz), 7.44(1H, d, J=2Hz), 7.60(1H, bs).<br>m.p.: 102.0–104.0° C.<br>Elemental analysis (%):<br>  Calc (%) C;66.79, H;7.21, N;5.56, Cl;14.08<br>  Found (%) C;66.45, H;7.40, N;5.77, Cl;13.79 |
| 3. | Cyclopropyl<br><br>CH₂\\<br>    CH—<br>CH₂/ | $IR\nu_{max}^{KBr}$ cm$^{-1}$: 3300, 1655.<br>$NMR\delta_{TMS}^{CCl_4}$: 0.70–1.00(4H, m), 1.22(6H, d, J=8Hz), 1.78(1H, m), 3.32(1H, m), 7.25(1H, d, J=8Hz), 7.46(1H, dd, J=8Hz, J=2Hz), 7.85(1H, d, J=2Hz), 9.55 (1H, bs).<br>m.p.: 112.0–114.0° C.<br>Elemental analysis (%):<br>  Calc (%) C;65.68, H;6.79, N;5.89, Cl;14.91<br>  Found (%) C;65.91, H;7.01, N;5.82, Cl;14.54 |

Examples are given below to illustrate the formulation of the herbicide of this invention and its herbicidal activity.

FORMULATION EXAMPLE 1

Wettable powder

Twenty parts by weight of compound No. 2, 2 parts by weight of sodium alkylbenzenesulfonate, 2 parts by weight of polyoxyethylene alkylphenyl ether and 76 parts by weight of Zieklite (trademark of Zieklite Chemical Industry Co., Ltd.; a carrier containing silica as a main ingredient) were well pulverized and mixed to form a wettable powder.

FORMULATION EXAMPLE 2

Wettable powder

Thirty parts by weight of compound No. 3, 6 parts by weight of polyoxyethylene alkylphenyl ether ammonium sulfate, 2 parts by weight of sodium naphthalenesulfonate/formaldehyde condensate, 1 part by weight of sodium alkylbenzenesulfonate, 2 parts by weight of polyvinyl alcohol and 59 parts by weight of diatomaceous earth were well pulverized to form a wettable powder.

FORMULATION EXAMPLE 3

Wettable powder

Fifty parts by weight of compound No. 2, 3 parts by weight of white carbon, 4 parts by weight of polyoxyethylene alkyl phenyl ether ammonium sulfate, 2 parts by weight of sodium alkylbenzenesulfonate and 41 parts by weight of diatomaceous earth were well pulverized and mixed to form a wettable powder.

FORMULATION EXAMPLE 4

Wettable powder

Fifty-five parts by weight of compound No. 1, 5 parts by weight of white carbon, 4 parts by weight of polyoxyethylene alkylphenyl ether ammonium sulfate, 2 parts by weight of sodium ligninsulfonate and 34 parts by weight of diatomaceous earth were well pulverized and mixed to form a wettable powder.

FORMULATION EXAMPLE 5

Wettable powder

Eighty parts by weight of compound No. 2, 5 parts by weight of white carbon, 7 parts by weight of polyoxyethylene alkylphenyl ether ammonium sulfate, 2 parts by weight of sodium naphthalenesulfonate/formaldehyde condensate, 2 parts by weight of sodium alkylbenzenesulfonate, and 4 parts by weight of diatomaceous earth were well pulverized and mixed to form a wettable powder.

FORMULATION EXAMPLE 6

Flowable agent

Water (76.7 parts by weight) was mixed with 20 parts by weight of compound No. 1, 2 parts by weight of sodium ligninsulfonate, 0.3 part by weight of xanthan gum and 1 part by weight of polyoxyethyelne alkylaryl ether, and the mixture was finely pulverized by a sand grinder to form a flowable agent.

FORMULATION EXAMPLE 7

Flowable agent

Water (52.8 parts by weight) was added to 40 parts by weight of compound No. 2, 3 parts by weight of sodium naphthalenesulfonate/formaldehyde condensate, 2 parts by weight of sodium ligninsulfonate, 0.1 part by weight of xanthan gum, 0.1 part by weight of Deltop (registered trademark of Takeda Chemical Co., Ltd.; industrial fungicide containing an organic iodine acetamide compound as a main active ingredient) and 2 parts by weight of polyoxyethylene alkylaryl ether, and the mixture was finely pulverized by a sand grinder to form a flowable agent.

FORMULATION EXAMPLE 8

Dust

Three parts by weight of compound No. 1, 3 parts by weight of sodium ligninsulfonate, 2 parts by weight of polyoxyethylene alkylaryl ether and 92 parts by weight of clay were mixed and pulverized to form a dust.

FORMULATION EXAMPLE 9

Dust

Twenty parts by weight of compound No. 2, 5 parts by weight of sodium ligninsulfonate, 4 parts by weight of polyoxyethylene alkylaryl ether and 71 parts by weight of clay were mixed and pulverized to form a dust.

FORMULATION EXAMPLE 10

Dry flowable agent

Sixty parts of compound No. 1, 5 parts by weight of sodium alkylbenzenesulfonate and 35 parts by weight of polypropylene glycol polyethylene glycol ether were finely pulverized by using a jet-O-miser to form a dry flowable agent.

FORMULATION EXAMPLE 11

Dry flowable agent

Seventy parts by weight of compound No. 2, 2 parts by weight of sodium alkylbenzenesulfonate, 18 parts by weight of polypropylene glycol polyethylene glycol ether and 10 parts by weight of white carbon were finely pulverized by using a jet-O-miser to form a dry flowable agent.

FORMULATION EXAMPLE 12

Granules

Finely pulverized compound No. 3 (20.5 parts by weight), 2.0 parts by weight of Gohsenol GL-5S (trademark of Nihon Synthetic Chemical Co., Ltd.; polyvinyl alcohol), 2.0 parts by weight of Sunexs P-252 (trademark of Sanyo Kokusaku Pulp Co., Ltd.; sodium ligninsulfonate) and 75.5 parts by weight of clay were well mixed, and then a suitable amount of water was added to wet the mixture. The mixture was then extruded by an injecting former to produce granules. The granules were air-dried at 60° to 70° C., crushed, and adjusted to a granule diameter of 0.3 to 1 mm by a size adjusting machine.

FORMULATION EXAMPLE 13

Granules

Five parts by weight of finely pulverized compound No. 2, 72 parts by weight of bentonite, 20 parts by weight of talc, 2 parts by weight of calcium dodecylbenzenesulfonate and 1 part by weight of calcium ligninsulfonate were well mixed, and a suitable amount of water was added to wet the mixture. The mixture was extruded by an injecting former to form granules. The granules were air-dried at 60° to 90° C., crushed and adjusted to a diameter of 0.5 to 1.2 mm.

FORMULATION EXAMPLE 14

Granules

Twelve parts by weight of finely pulverized compound No. 1, 60 parts by weight of bentonite, 25 parts by weight of talc, 2 parts by weight of sodium naphthalenesulfonate/formaldehyde condensate and 1 part by weight of dioctyl sulfosuccinate were well mixed, and a suitable amount of water was added to wet the mixture. The mixture was extruded by an injecting former to form granules. The granules were air-dried at 60° to 90° C., crushed, and adjusted to a diameter of 0.3 to 1 mm.

FORMULATION EXAMPLE 15

Emulsifiable concentrate

Ten parts by weight of compound No. 2, 10 parts by weight of Sorpol 800A (trademark of Toho Chemical Co., Ltd.; a mixture of nonionic and anionic surfactants) and 80 parts by weight of benzene were mixed and dissolved to form an emulsifiable concentrate.

FORMULATION EXAMPLE 16

Emulsifiable concentrate

Fifty parts by weight of compound No. 1, 15 parts by weight of Gafac RS-610 (trademark of General Aniline & Film Corporation; polyoxyethylene phosphate) and 35 parts by weight of o-xylene were mixed and dissolved to form an emulsifiable concentrate.

D: N-(3,4-dichlorophenyl)methacrylamide (dicryl) [British Pat. No. 885,043]

TABLE 2

| Compound | Concentration × 1,000 ppm | Weed | | | | | | | | | | | | Crop | | | | |
|---|---|---|---|---|---|---|---|---|---|---|---|---|---|---|---|---|---|---|
| | | (a) | (b) | (c) | (d) | (e) | (f) | (g) | (h) | (i) | (j) | (k) | (l) | Rice | Wheat | Corn | Peanut | Soybean |
| A | 1 | 4 | 5 | 3 | 1 | 3 | 5 | 4 | 5 | 5 | 5 | 2 | 2 | 0 | 2 | 1 | 2 | 2 |
| | 2 | 5 | 5 | 4 | 2 | 4 | 5 | 5 | 5 | 5 | 5 | 3 | 3 | 1 | 3 | 1 | 2 | 3 |
| | 5 | 5 | 5 | 5 | 2 | 4 | 5 | 5 | 5 | 5 | 5 | 5 | 4 | 1 | 3 | 3 | 3 | 4 |
| B | 1 | 3 | 5 | 4 | 0 | 2 | 4 | 4 | 5 | 4 | 5 | 2 | 3 | 2 | 1 | 1 | 1 | 1 |
| | 2 | 5 | 5 | 4 | 2 | 2 | 5 | 5 | 5 | 5 | 5 | 3 | 4 | 2 | 3 | 2 | 2 | 2 |
| | 5 | 5 | 5 | 5 | 2 | 3 | 5 | 5 | 5 | 5 | 5 | 4 | 5 | 3 | 3 | 3 | 3 | 3 |
| C | 1 | 3 | 4 | 3 | 0 | 2 | 5 | 4 | 5 | 4 | 5 | 2 | 2 | 2 | 2 | 1 | 1 | 1 |
| | 2 | 5 | 5 | 5 | 1 | 2 | 5 | 5 | 5 | 4 | 5 | 3 | 2 | 3 | 2 | 2 | 2 | 2 |
| | 5 | 5 | 5 | 5 | 2 | 3 | 5 | 5 | 5 | 5 | 5 | 4 | 3 | 3 | 3 | 3 | 3 | 2 |
| D | 1 | 3 | 4 | 3 | 0 | 2 | 5 | 4 | 4 | 4 | 4 | 2 | 2 | 2 | 2 | 1 | 1 | 2 |
| | 2 | 4 | 5 | 3 | 1 | 3 | 5 | 5 | 5 | 4 | 5 | 3 | 2 | 3 | 3 | 3 | 2 | 3 |
| | 5 | 5 | 5 | 5 | 1 | 3 | 5 | 5 | 5 | 5 | 5 | 4 | 3 | 3 | 3 | 3 | 3 | 3 |
| Compound No. 1 of this invention | 1 | 4 | 5 | 4 | 3 | 5 | 5 | 5 | 5 | 5 | 5 | 5 | 5 | 2 | 0 | 1 | 0 | 2 |
| | 2 | 5 | 5 | 5 | 3 | 5 | 5 | 5 | 5 | 5 | 5 | 5 | 5 | 2 | 0 | 2 | 1 | 2 |
| | 5 | 5 | 5 | 5 | 4 | 5 | 5 | 5 | 5 | 5 | 5 | 5 | 5 | 3 | 1 | 2 | 2 | 3 |

FORMULATION EXAMPLE 17

Emulsifiable concentrate

Twenty-five parts of compound No. 1, 15 parts by weight of Plysurf A-210G (trademark of Dai-ichi Kogyo Seiyaku Co., Ltd.; polyoxyethylene phosphate) and 60 parts by weight of o-xylene were mixed and dissolved to form an emulsifiable concentrate.

TEST EXAMPLE 1

Plastic pots (1/10,000 a) were filled with the soil taken from an upland farm, and seeds of one kind of test plant were sown in each pot and grown in a greenhouse. When each plant grew to a stage of 2 or 3 leaves, each of the test compounds was dissolved in acetone containing polyoxyethylene sorbitan monooleate and sorbitan monolaurate. The solution was sprayed by a pressure micro-sprayer at a rate of 2 kiloliters per hectare. On the 21st day after the spraying of the chemical, the effects of the chemical on the crops and weeds were observed and examined. The results are shown in Table 2. The degree of injury to the test plants was evaluated on the following scale.

| Rating | Degree of injury (%) | State of the injury |
|---|---|---|
| 5 | 100 | Withered (complete control of weeds) |
| 4 | 80 | Enormous injury (80% weed control) |
| 3 | 60 | Medium injury (60% weed control) |
| 2 | 40 | Small injury (40% weed control) |
| 1 | 20 | Slight injury (20% weed control) |
| 0 | 0 | No injury (no weed control) |

The control compounds shown in Table 2 were as follows:

A: N-(3,4-dichlorophenyl)propionamide (propanil)
B: N-(3,4-dichlorophenyl)-2-methylpentanamide (karsil) [British Pat. No. 869,169]
C: N-(3-chloro-4-methylphenyl)-2-methylpentanamide (solan) [British Pat. No. 869,169]

TEST EXAMPLE 2

A plastic planter (1/1,000 a) was filled with the soil from an upland farm, and seeds of wild oats, water foxtail, annual bluegrass, chickweeed, lamb's quarters and black bindweed as weeds were sown in the planter. Simultaneously, seeds of wheat (variety: Norin No. 61) and barley (variety: Tochigi Sekitori No. 1) as crops were sown in the planter. These plants were cultivated in a phytotron (12°-18° C.) When wheat grew to a stage of 2 or 3 leaves, a predetermined amount of each of the test compounds formulated as in Formulation Example 15 was diluted with water in an amount corresponding to 500 liters per hectare, and applied by a microsprayer. In the third week after the treatment with the chemical, the effects of the chemical on the weeds and crops were observed and evaluated. The results are shown in Table 3. The degree of injury to the test plants was rated as in Test Example 1.

The control compounds indicated in Table 3 were as follows:

E: N-(4-isopropylphenyl)-2-methyl-2-pentenamide (Japanese Laid-Open Patent Publication No. 23357/1985)
F: N-(3-chloro-4-isopropylphenyl)propionamide (West German Pat. No. 2,249,547)
G: N-(3-chloro-4-methyphenyl)-2-methyl-2-pentenamide (British Pat. No. 885,043)

TABLE 3

| Compound | Concentration × 1,000 ppm | Weed | | | | | | | Crop | |
|---|---|---|---|---|---|---|---|---|---|---|
| | | (d) | (m) | (e) | (h) | (g) | (i) | (n) | Wheat | Barley |
| E | 1 | 0 | 2 | 2 | 2 | 5 | 1 | 2 | 0 | 0 |
| | 2 | 1 | 3 | 3 | 3 | 5 | 2 | 4 | 0 | 0 |
| | 4 | 2 | 3 | 4 | 4 | 5 | 3 | 4 | 0 | 0 |
| F | 1 | 1 | 1 | 1 | 2 | 3 | 2 | 1 | 1 | 1 |
| | 2 | 1 | 1 | 2 | 2 | 5 | 2 | 2 | 2 | 2 |
| | 4 | 2 | 2 | 3 | 4 | 5 | 3 | 3 | 2 | 3 |
| G | 1 | 1 | 2 | 2 | 2 | 5 | 1 | 2 | 1 | 1 |
| | 2 | 1 | 3 | 3 | 3 | 5 | 3 | 3 | 2 | 2 |
| | 4 | 1 | 3 | 4 | 4 | 5 | 4 | 3 | 3 | 2 |
| Compound No. 1 of this invention | 1 | 3 | 4 | 4 | 5 | 5 | 5 | 4 | 0 | 0 |
| | 2 | 4 | 4 | 5 | 5 | 5 | 5 | 5 | 0 | 0 |
| | 4 | 5 | 5 | 5 | 5 | 5 | 5 | 5 | 0 | 0 |

TABLE 3-continued

| Compound | Concentration × 1,000 ppm | Weed (d) | (m) | (e) | (h) | (g) | (i) | (n) | Crop Wheat | Barley |
|---|---|---|---|---|---|---|---|---|---|---|
| tion | | | | | | | | | | |

| Standards of evaluation (survival rate based on the air-dried weight in the non-treated area) | |
|---|---|
| 0: | 91–100% |
| 1: | 61–90% |
| 2: | 36–60% |
| 3: | 11–35% |
| 4: | 6–10% |
| 5: | 0–5% |

TEST EXAMPLE 3

A planter having a capacity of 1/1000 a was filled with soil, and seeds of wheat, wild oats, meadow foxtail, black grass, water foxtail, annual bluegrass, pick purse, As the control methabenzthiazuron, diclofopmethyl and propanil, a commercial tribunil wettable powder, a commercial Hoelon emulsiable concentrate and a commercial stam emulsifiable concentrate were used.

TABLE 4

| Compound | Rate of application of the active ingredient (g/a) | Crop Wheat | Weed (d) | (o) | (p) | (m) | (e) | (q) | (r) | (g) | (h) | (s) | (t) | (u) |
|---|---|---|---|---|---|---|---|---|---|---|---|---|---|---|
| Compound No. 1 of this invention | 2.5 | 0 | 5 | 5 | 4 | 5 | 5 | 5 | 5 | 5 | 4 | 5 | 4 | 5 |
| | 5 | 0 | 5 | 5 | 5 | 5 | 5 | 5 | 5 | 5 | 5 | 5 | 5 | 5 |
| | 10 | 0 | 5 | 5 | 5 | 5 | 5 | 5 | 5 | 5 | 5 | 5 | 5 | 5 |
| (Control) H | 10 | 0 | 0 | 0 | 0 | 0 | 0 | 4 | 3 | 4 | 5 | 4 | 3 | 4.5 |
| | 20 | 0 | 0 | 0 | 1 | 0 | 2 | 5 | 4.5 | 4 | 5 | 5 | 5 | 5 |
| | 30 | 0.5 | 0 | 2 | 2 | 1.5 | 3 | 5 | 5 | 5 | 5 | 5 | 5 | 5 |
| I | 5 | 0 | 4 | 4 | 2 | 4 | 4 | 0 | 0 | 0 | 0 | 0 | 0 | 0 |
| | 10 | 0 | 5 | 5 | 3 | 4 | 5 | 0 | 1 | 0 | 0 | 0 | 1 | 1 |
| | 20 | 1 | 5 | 5 | 5 | 5 | 5 | 0 | 1.5 | 1 | 1 | 0 | 1 | 2 |
| J | 2.5 | 0 | 3 | 3 | 2 | 2 | 2 | 3 | 3 | 4 | 2 | 2 | 2 | 2 |
| | 5 | 0 | 3 | 3 | 3 | 3 | 3 | 4 | 3.5 | 5 | 3 | 3 | 2 | 3 |
| | 10 | 0 | 5 | 4 | 4 | 4 | 4 | 5 | 4.5 | 5 | 5 | 3 | 3 | 3 |
| K | 5 | 2 | 3 | 2 | 1 | 2 | 1 | 3 | 3 | 3.5 | 3 | 3 | 3 | 3 |
| | 10 | 3 | 3 | 3 | 3 | 3 | 4 | 4 | 4.5 | 4 | 3.5 | 3.5 | 3.5 | 4 |
| | 20 | 4 | 4 | 4 | 4 | 3.5 | 4.5 | 4.5 | 5 | 5 | 5 | 4.5 | 5 | 4.5 |
| A | 2.5 | 2.5 | 2 | 2 | 2 | 2 | 2 | 3 | 3 | 3 | 2 | 2 | 3 | 1 |
| | 5 | 3 | 3 | 4 | 3 | 3.5 | 3.5 | 3.5 | 4 | 4 | 4 | 4 | 3 | 3 |
| | 10 | 3 | 4 | 4 | 3 | 4 | 4 | 5 | 5 | 4.5 | 5 | 4 | 4 | 4 | cleavers, lamb's quarters, dead nettle, *Cerastium holosteoides, Veronica caninotesticulate,* and chickweed were sown, and grown in a greenhouse. When the test plants grew to the 2- to 3-leaf stage, a predetermined amount of a flowable agent prepared as in Formulation Example 6 was diluted with water in an amount corresponding to 10 liters per are, and the dilution was sprayed by a microsprayer. Thirty days after the treatment, the state of growth of the crop and the weeds was examined, and the results shown in Table 4 were obtained.

In Table 4, the degree of phytotoxicity to the crop and the herbicidal efficacy on the weeds are expressed on the following standards of evaluation by comparing the state of growth of the crop or weed with the air-dried amount of the crop or weed in the nontreated area.

H: 3-(2-benzothiazolyl)-1,3-dimethylurea (methabenzthiazuron)

I: methyl(±)-2-4-(2,4-dichlorophenoxy)phenoxy)-propionate (diclofop-methyl)

J: N-(4-isopropylphenyl)-2-methyl-2-pentenamide (Japanese Laid-Open Patent Publication No. 23357/1985)

K: N-(3,4-dichlorophenyl)-2-bromo-2-methylvaleramide (Japanese Patent Publication No. 14240/1966)

TEST EXAMPLE 4

Compound No. 3 of the invention was subjected to a herbicidal activity test in accordance with the method of Test Example 1. The results given in Table 5 was obtained. As a control compound, N-(3,4-dichlorophenyl)cyclopropanecarboxamide (L) (cypromid; U.S. Pat. No. 3,272,107) was used instead of N-(3-chloro-4-methylphenyl)-2-methylpentanamide (c).

TABLE 5

| Compound | Concentration × 1,000 ppm | Weed (a) | (b) | (c) | (d) | (e) | (f) | (g) | (h) | (i) | (j) | (k) | (l) | Crop Rice | Wheat | Corn | Peanut | Soybean |
|---|---|---|---|---|---|---|---|---|---|---|---|---|---|---|---|---|---|---|
| A | 1 | 4 | 5 | 3 | 1 | 3 | 5 | 3 | 5 | 4 | 5 | 2 | 2 | 0 | 2 | 1 | 1 | 2 |
| | 2 | 5 | 5 | 5 | 2 | 3 | 5 | 4 | 5 | 5 | 5 | 4 | 3 | 1 | 3 | 2 | 2 | 3 |
| | 5 | 5 | 5 | 5 | 3 | 4 | 5 | 5 | 5 | 5 | 5 | 5 | 4 | 2 | 3 | 3 | 3 | 4 |
| B | 1 | 3 | 3 | 4 | 0 | 2 | 4 | 4 | 4 | 4 | 5 | 2 | 3 | 2 | 1 | 1 | 1 | 1 |
| | 2 | 5 | 4 | 4 | 1 | 3 | 5 | 4 | 5 | 5 | 5 | 3 | 4 | 2 | 3 | 2 | 3 | 2 |
| | 5 | 5 | 5 | 5 | 2 | 3 | 5 | 5 | 5 | 5 | 5 | 4 | 5 | 3 | 4 | 3 | 3 | 3 |
| L | 1 | 3 | 4 | 3 | 1 | 2 | 5 | 4 | 5 | 4 | 5 | 2 | 2 | 2 | 2 | 2 | 1 | 2 |
| | 2 | 5 | 4 | 5 | 3 | 3 | 5 | 5 | 5 | 4 | 5 | 3 | 4 | 3 | 2 | 3 | 2 | 2 |
| | 5 | 5 | 5 | 5 | 3 | 3 | 5 | 5 | 5 | 5 | 5 | 4 | 5 | 3 | 3 | 3 | 3 | 3 |
| D | 1 | 3 | 4 | 3 | 0 | 2 | 5 | 4 | 4 | 4 | 4 | 2 | 3 | 2 | 2 | 2 | 1 | 3 |
| | 2 | 4 | 5 | 4 | 1 | 3 | 5 | 5 | 5 | 5 | 4 | 3 | 3 | 3 | 2 | 3 | 2 | 4 |
| | 5 | 5 | 5 | 5 | 2 | 3 | 5 | 5 | 5 | 5 | 5 | 5 | 4 | 4 | 3 | 3 | 3 | 5 |

TABLE 5-continued

| Compound | Concentration × 1,000 ppm | Weed | | | | | | | | | | | | Crop | | | | |
|---|---|---|---|---|---|---|---|---|---|---|---|---|---|---|---|---|---|---|
| | | (a) | (b) | (c) | (d) | (e) | (f) | (g) | (h) | (i) | (j) | (k) | (l) | Rice | Wheat | Corn | Peanut | Soybean |
| Compound No. 3 of this invention | 1 | 5 | 5 | 3 | 2 | 4 | 5 | 5 | 5 | 5 | 5 | 4 | 4 | 2 | 0 | 1 | 1 | 1 |
| | 2 | 5 | 5 | 5 | 4 | 4 | 5 | 5 | 5 | 5 | 5 | 4 | 4 | 2 | 0 | 1 | 1 | 2 |
| | 5 | 5 | 5 | 5 | 4 | 5 | 5 | 5 | 5 | 5 | 5 | 5 | 5 | 3 | 1 | 2 | 2 | 3 |

TEST EXAMPLE 5

Compound No. 2 of this invention was subjected to a herbicidal activity test in accordance with the method of Test Example 2. The results given in Table 6 were obtained. As a control compound, N-(3,4-dichlorophenyl) 1-methylcyclopropanecarboxamide (M) (U.S. Pat. No. 3,277,171) was used instead of N-(3-chloro-4-methylphenyl)-2-methylpentenamide (G).

TABLE 6

| Compound | Concentration × 1,000 ppm | Weed | | | | | | | Crop | |
|---|---|---|---|---|---|---|---|---|---|---|
| | | (d) | (m) | (e) | (h) | (g) | (i) | (n) | Wheat | Barley |
| E | 1 | 0 | 2 | 2 | 2 | 5 | 1 | 2 | 0 | 0 |
| | 2 | 0 | 2 | 3 | 3 | 5 | 2 | 3 | 0 | 0 |
| | 4 | 1 | 3 | 4 | 4 | 5 | 4 | 4 | 0 | 0 |
| F | 1 | 1 | 1 | 1 | 2 | 3 | 1 | 1 | 1 | 1 |
| | 2 | 1 | 2 | 2 | 2 | 5 | 2 | 2 | 2 | 2 |
| | 4 | 2 | 2 | 3 | 4 | 5 | 2 | 3 | 2 | 3 |
| M | 1 | 1 | 2 | 2 | 2 | 4 | 3 | 2 | 1 | 1 |
| | 2 | 2 | 3 | 3 | 3 | 5 | 3 | 3 | 2 | 2 |
| | 4 | 2 | 4 | 4 | 4 | 5 | 4 | 3 | 2 | 2 |
| Compound No. 2 of this invention | 1 | 3 | 3 | 4 | 5 | 5 | 5 | 3 | 0 | 0 |
| | 2 | 4 | 4 | 5 | 5 | 5 | 5 | 4 | 0 | 0 |
| | 4 | 5 | 5 | 5 | 5 | 5 | 5 | 5 | 0 | 1 |

TEST EXAMPLE 6

Compounds Nos. 2 and 3 of this invention were subjected to a herbicidal activity test in accordance with the method of Test Example 3. The results given in Table 7 were obtained.

The plants shown by alphabets in Tables 2 to 7 were as follows:

| | English | Scientific nomenclature |
|---|---|---|
| (a) | crabgrass | Digitaria cilialis |
| (b) | green foxtail | setaria viridis |
| (c) | barnyard grass | Echinochloa oryzicola |
| (d) | wild oats | Avena fatua L. |
| (e) | annual bluegrass | Poa annua L. |
| (f) | green amaranth | Amaranthus retroflexus |
| (g) | lamb's quarters | Chenopodium album |
| (h) | chickweed | Stellaria media |
| (i) | charlock | Sinapis arvensis |
| (j) | black bindweed | Polygonum convolvulus |
| (k) | cocklebur | Xanthium strumarium |
| (l) | morning glory | Ipomea purpurea |
| (m) | water foxtail | Alopecurus aequalis |
| (n) | matricaria | Matricaria chamomilla |
| (o) | meadow foxtail | Alopecurus pratensis |
| (p) | black grass | Alopecurus myosuroides |
| (q) | pick purse | Capsella bursapastoris |
| (r) | cleavers | Galium spurium |
| (s) | henbit | Lamium amplexicaule |
| (t) | — | Cerastium holosteoides |
| (u) | — | Veronica caninotesticulata |

The foregoing test results demonstrate that the herbicides containing the compounds the compounds of this invention have a marked herbicidal efficacy at low dosages against all weeds tested by a foliar treatment not affected by the soil while showing outstanding selectivity for useful gramineous crops, particularly wheat, and that they excell the control chemicals (such as methabenzthiazuron, propanil, karsil, etc.) or other known compounds.

What is claimed is:

1. N-(3-chloro-4-isopropylphenyl) carboxamide represented by the formula (I):

TABLE 7

| Compound | Rate of application of the active ingredient (g/a) | Crop Wheat | Weed | | | | | | | | | | |
|---|---|---|---|---|---|---|---|---|---|---|---|---|---|
| | | | (d) | (o) | (p) | (m) | (e) | (q) | (r) | (g) | (h) | (s) | (t) | (u) |
| 2 | 2.5 | 0 | 4 | 5 | 4 | 4 | 5 | 4 | 4 | 4 | 4 | 4 | 4 | 4 |
| | 5 | 0 | 5 | 5 | 5 | 5 | 5 | 5 | 5 | 5 | 5 | 5 | 5 | 5 |
| | 10 | 1 | 5 | 5 | 5 | 5 | 5 | 5 | 5 | 5 | 5 | 5 | 5 | 5 |
| 3 | 2.5 | 0 | 4 | 4 | 5 | 4 | 4 | 5 | 5 | 5 | 4 | 4 | 5 | 5 |
| | 5 | 0 | 5 | 5 | 5 | 5 | 5 | 5 | 5 | 5 | 5 | 5 | 5 | 5 |
| | 10 | 1 | 5 | 5 | 5 | 5 | 5 | 5 | 5 | 5 | 5 | 5 | 5 | 5 |
| (Control) H | 10 | 0 | 0 | 0 | 0 | 0 | 0 | 4 | 3 | 4 | 5 | 4 | 4 | 4.5 |
| | 20 | 0 | 0 | 0 | 0 | 0 | 2 | 5 | 4 | 5 | 5 | 5 | 5 | 5 |
| | 30 | 0.5 | 0 | 2 | 1 | 1.5 | 2 | 5 | 5 | 5 | 5 | 5 | 5 | 5 |
| I | 5 | 0 | 4 | 4 | 2 | 4 | 4 | 0 | 0 | 0 | 0 | 0 | 0 | 0 |
| | 10 | 0 | 5 | 5 | 4 | 4 | 5 | 0 | 1 | 0 | 1 | 0 | 0 | 1 |
| | 20 | 1 | 5 | 5 | 5 | 5 | 5 | 1 | 1.5 | 1 | 2 | 0 | 1 | 2 |
| J | 2.5 | 0 | 3 | 3 | 3 | 2 | 3 | 3 | 3 | 4 | 2 | 2 | 2 | 2 |
| | 5 | 0 | 3 | 3 | 3 | 3 | 4 | 4 | 3.5 | 5 | 3 | 3 | 2 | 3 |
| | 10 | 0 | 5 | 4 | 4 | 4 | 4 | 5 | 5 | 5 | 3 | 3 | 3 | 3 |
| K | 5 | 2 | 2 | 2 | 1 | 2 | 2 | 3 | 3 | 3.5 | 3 | 3 | 3 | 3 |
| | 10 | 3 | 3 | 3 | 3 | 3 | 3 | 4 | 4.5 | 4 | 4 | 3.5 | 4 | 4 |
| | 20 | 4 | 4 | 4 | 4 | 3.5 | 4.5 | 4.5 | 5 | 5 | 5 | 4.5 | 5 | 4.5 |
| A | 2.5 | 2 | 2 | 2 | 2 | 2 | 2 | 3 | 3 | 3 | 2 | 2 | 3 | 2 |
| | 5 | 3 | 3 | 4 | 3 | 4 | 3.5 | 4 | 4 | 3 | 3 | 4 | 4 | 3 |
| | 10 | 3 | 4 | 4 | 3 | 4 | 4.5 | 5 | 5 | 4.5 | 5 | 4 | 4 | 4 |

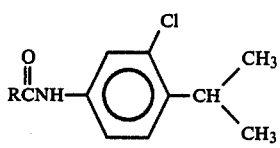
wherein R represents a 1-methylbutyl group.
2. A selective herbicide comprising a herbicidally effective amount of N-(3-chloro-4-isopropylphenyl) carboxamide represented by the formula (I):
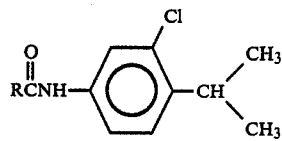
wherein R represents a 1-methylbutyl group as an active ingredient, a carrier and/or at least one adjuvant.
* * * * *